United States Patent [19]

Howson

[11] Patent Number: 4,722,733

[45] Date of Patent: Feb. 2, 1988

[54] DRUG HANDLING APPARATUS AND METHOD

[75] Inventor: David C. Howson, Denver, Colo.

[73] Assignee: Intelligent Medicine, Inc., Denver, Colo.

[21] Appl. No.: 833,067

[22] Filed: Feb. 26, 1986

[51] Int. Cl.[4] ............................................. A61M 5/16

[52] U.S. Cl. ..................................... 604/411; 604/89; 141/330

[58] Field of Search ................. 604/411, 416, 406, 88, 604/89, 92, 201, 405; 141/19, 329, 330, 286

[56] References Cited

U.S. PATENT DOCUMENTS

| | | | |
|---|---|---|---|
| 1,929,616 | 10/1933 | Vopata . | |
| 2,668,533 | 2/1954 | Evans . | |
| 2,812,117 | 11/1957 | Butkus et al. . | |
| 3,125,092 | 3/1964 | Cohen . | |
| 3,337,041 | 8/1967 | Damaskus . | |
| 3,359,977 | 12/1967 | Burke . | |
| 3,662,752 | 5/1972 | Yokoyama . | |
| 3,783,895 | 1/1974 | Weichselbaum . | |
| 3,797,521 | 3/1974 | King . | |
| 3,881,640 | 5/1975 | Noble . | |
| 3,938,520 | 2/1976 | Scislowicz et al. . | |
| 4,211,588 | 7/1980 | Raines . | |
| 4,410,321 | 10/1983 | Pearson et al. . | |
| 4,505,709 | 3/1985 | Froning et al. . | |
| 4,543,101 | 9/1985 | Crouch | 604/411 |
| 4,564,054 | 1/1986 | Gustausson | 604/198 X |
| 4,576,211 | 3/1986 | Valentini et al. | 604/88 |

*Primary Examiner*—John D. Yasko
*Attorney, Agent, or Firm*—Robert E. Harris

[57] ABSTRACT

A drug handling apparatus and method are disclosed. A delivery receptacle, such as a syringe, is provided with a first substance, such as a liquid diluent, either stored in the delivery receptacle or provided from a separate storage receptacle, and the first substance in the delivery receptacle is transferred to a storage receptacle provided with a second substance, such as a drug in solid form, with the transfer being accomplished by moving an actuator, such as the piston within a syringe, in a first direction to create a positive flow of the first substance from the delivery receptacle through a vented transfer unit to the storage receptacle where the substances are mixed to thereby, for example, reconstitute the drug. By then moving the actuator in a second direction, such as by movment of the syringe piston in the opposite axial direction, the mixture is then withdrawn from the storage receptacle and transferred through the vented transfer unit to the delivery receptacle. After removal of the storage receptacle and transfer unit from the delivery receptacle, the mixture can then be discharged from the delivery receptacle to a patient connected therewith by again actuating the actuator in the first direction. Packaging for the delivery and storage receptacles is provided with the receptacles being stored in spaced and sealed relationship until needed.

16 Claims, 10 Drawing Figures

DRUG HANDLING APPARATUS AND METHOD

FIELD OF THE INVENTION

This invention relates to a substance handling apparatus and method, and, more particularly, relates to a drug handling apparatus and method.

BACKGROUND OF THE INVENTION

It is well known that various substances can, or must, be packaged for use at a later time and/or place. This is particularly true, for example, with respect to drugs, and various attempts have been heretofore made to package drugs with a view toward overcoming the many problems associated therewith.

Heretofore, it has been quite common, for example, in pre-filled drug packaging, to provide unit doses wherein the entire contents of the prepared package are delivered to the patient with no attempt being made to individualize the dosage.

Known devices and methods for providing and/or utilizing pre-filled drug packages, however, have heretofore required significant manual labor, particularly in administering the contents, even though preparation time was often reduced relative to non-pre-filled packages, and most known packaging for injectable drugs has not been designed for integration with delivery control devices that allow multiple doses to be administered to a patient.

Traditional multi-dose containers have, typically, been intended for reconstitution with diluent and dispensing from separate containers, each of which had to be filled with the drug solution. Normally these containers have been simple bottles using a needle penetration septum, and separate venting has been commonly utilized, such as that provided by self-venting filters or by a separate needle.

While self-venting filters/needles have been intended to allow safe use of multi-dose or unit dose vials by trapping aerosols released when the access needle is withdrawn from the septum, the use of this separate component, along with the others needed to actually have a drug available to deliver, increased the cost and time of preparation.

Self-dispensing (i.e., piggy-back) bottles has been another heretofore suggested approach. Bottles of this type have normally contained only enough drug for a single dose, and the drug has usually been reconstituted using a separate source of diluent and preparative supplies. When the drug has been reconstituted in such a bottle, the bottle itself has then served as the dispensing reservoir for the dose, with such dispensing being normally under gravity flow.

A variation of the self-dispensing bottle approach, that has also been heretofore suggested was a soft bag pre-filled with a dry drug. While having the same general objective, a diluent dispenser has been utilized to speed up the process of filling the bag for reconstitution.

A still different approach heretofore suggested was utilization of a partial-fill bag wherein the bag contains diluent. Separate supplies have normally been used to reconstitute the drug, which was then added to the partially filled bag, to make a unit dose. In a sophistication of this approach, a dry drug vial has been utilized with the vial attached to a special partial-fill bag to eliminate the need for preparation supplies and extra diluent.

To save preparation time, it has also been suggested that bags be provided that are pre-filled with drug solution, usually to be stored frozen. Another unit dose pre-fill approach that has been suggested was a pre-filled syringe cartridge which contains drug solution. A drug pre-fill has also been suggested containing a drug which could be inserted into a special patient-activated delivery pump.

All of the unit dose approaches, however, have had the clear limitation of being applicable only to those drugs which are given in the same dose (i.e., quantity of drug), or within a very small range of doses, to most patients. It can therefore be appreciated that multi-dose packaging, on the other hand, can present substantial advantages if the contents can be custom-dispensed without significant labor input.

A major problem with any liquid pre-fill, however, regardless of whether delivery is intended as a unit dose or a multi-dose, is that such pre-fills have heretofore been commonly limited either to those drugs which are stable at room temperatures or are frozen. This can be overcome, however, by the use of dry or binary (dry chamber plus diluent chamber) packaging forms, since such packaging allows continued separation of the drug components until near the time of use, at which time the components can be mixed and dispensed. This clearly is advantageous, particularly where the components should not (or perhaps in some cases cannot) be mixed until quite near the time of intended use, such as, for example, where the reconstituted drug has a short shelf-life.

With respect to prior art patents, U.S. Pat. No. 3,938,520 is directed to a mixing device having a vented transfer unit wherein the contents of a medicament storage receptacle can be mixed with the contents of a diluent storage receptacle with the lower positioned diluent storage receptacle being vented through the transfer unit positioned above the diluent storage unit, and with a syringe being mentioned for withdrawal of the mixture from the diluent stage receptacle, while still in the upright position, through the transfer unit.

U.S. Pat. No. 3,125,092 is directed to a device for supplying an additive material to a solution in an infusion flask by withdrawing solution from the infusion flask through a needle using a rubber ball positioned between the needle and container holding the additive material, mixing the withdrawn solution with additive material in the additive container, and then exerting positive pressure to return the mixture through the needle to the infusion flask.

U.S. Pat. No. 4,410,321 is directed to a closed drug delivery system wherein the diluent is within a bag and is mixed at the bag with a substance stored in a separate container prior to use.

U.S. Pat. No. 3,337,041 is directed to a disposable syringe wherein material, in solid state within the syringe, is mixed in the syringe with liquid material withdrawn from a storage receptacle by insertion of the nozzle end of the syringe into the storage receptacle.

U.S. Pat. No. 1,929,616 is directed to a double compartment ampule wherein two substances are mixed within the ampule by repositioning a divider between the compartments separately storing the substances.

U.S. Pat. No. 3,881,640 is directed to a measuring means for reconstituted substances with the device having an air vent filter connected therewith for venting air from the top portion of the measuring means. U.S. Pat. No. 3,938,520, discussed above, also includes a filter included in the air vent passage above the receptacle being vented.

As can be appreciated from the foregoing, while various devices and methods have heretofore been suggested and/or utilized for handling of various substances, including handling of drugs with mixing of such drugs being included in such handling, such devices and methods have not proved to be completely successful, at least in some cases, in providing a device and method for handling substances, such as drugs, particularly where such drugs are to be used in individualized doses, are to be mixed just prior to use, and/or are to be prepared and utilized with minimum labor, minimum chance of error occurrence, and maximum safety.

SUMMARY OF THE INVENTION

This invention provides an improved device and method for handling substances, and particularly drugs, with individualized dosage being made possible, with mixing occurring just prior to use, with labor and the chance of error occurrence being minimized, and with safety being maximized.

In this invention, the delivery receptacle is provided with an actuator therein, and has a first substance, such as a diluent, inserted into the delivery receptacle. The first substance in the delivery receptacle is moved by positive flow, due to actuation of the actuator in the delivery receptacle, through a vented transfer unit to a storage receptacle having a second substance, such as a drug, therein for mixing thereat. The mixture is thereafter withdrawn by actuation of the actuator and caused to flow through the transfer unit to the delivery receptacle, with delivery of the mixture to a patient being thereafter caused by actuation of the actuator, after the storage receptacle and transfer unit have been removed from the delivery receptacle.

It is therefore an object of this invention to provide an improved apparatus and method for handling substances.

It is another object of this invention to provide an improved apparatus and method for handling drugs, including mixing prior to use.

It is still another object of this invention to provide an improved apparatus and method for handling substances in a safe manner with minimum labor being required.

It is still another object of this invention to provide an improved apparatus and method for handling drugs to enable individualized dosage.

It is still another object of this invention to provide an improved apparatus and method for handling substances wherein a delivery receptacle is utilized during processing as well as delivery.

It is still another object of this invention to provide an improved apparatus and method for handling substances wherein a diluent is provided in a delivery receptacle, wherein the diluent is transferred through a transfer unit to a storage receptacle containing a drug, wherein the mixture is transferred through the transfer unit to the delivery receptacle, and wherein the delivery receptacle can then be utilized to deliver the mixture to a patient.

It is still another object of this invention to provide an improved apparatus and method for handling substances wherein the necessary elements are packaged and sealed until use.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompany drawings illustrate a complete embodiment of the invention according to the best mode so far devised for the practical application of the principles thereof, and in which.

DESCRIPTION OF THE INVENTION

Figure 1:
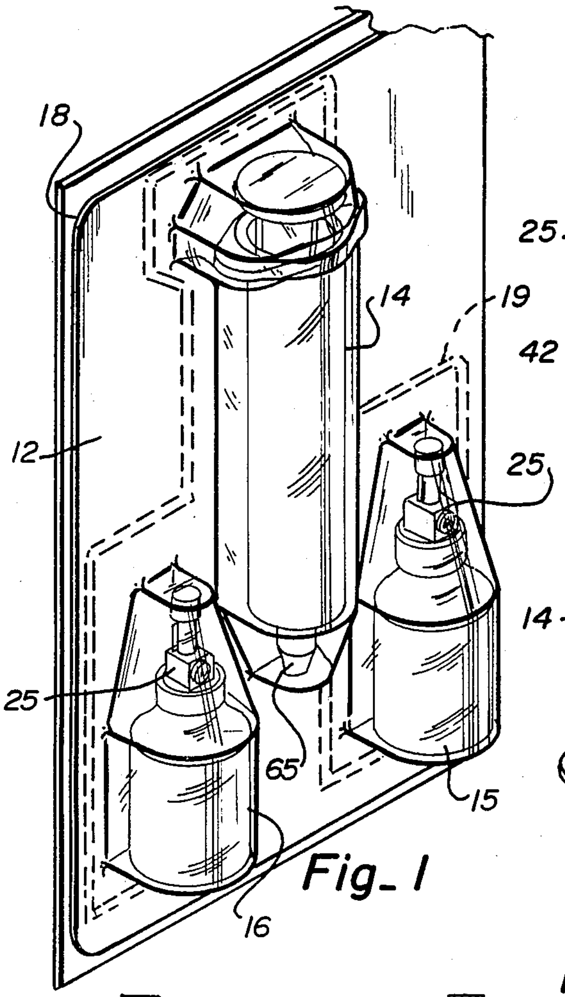
FIG. 1 is a perspective view of a sealed package utilized to package components until use.

Referring to FIG. 1, a sealed package 12 is illustrated containing the components, or elements, needed for utilization, with the components to be provided to a user being therefore within a sealed envelope which can be left intact until needed for use.

As indicated in FIG. 1, when package 12 is used to package drug components, the package can typically include a delivery receptacle 14, a first substance storage receptacle 15, and a second substance storage receptacle 16. When so provided, the receptacles are preferably held in spaced relationship with respect to one another with the package being sealed around edges 18 by conventional means, and with sealed pockets also being preferably formed around each component to separately hold each component within a separate compartment, which compartments are formed by seals 19.

The packaging material can be conventional, and can be, for example, sealable foil material. When sealed (as by conventional heat sealing, for example), the package forms a vapor-barrier envelope to maintain the components in a sterile, dry environment until the package is opened, typically at the time of intended use.

While the package shown herein contains three specific receptacles, it is meant to be realized that the number and form of the receptacles can be varied as needed for a particular use, and the invention is not meant to be limited thereto.

Figure 3:
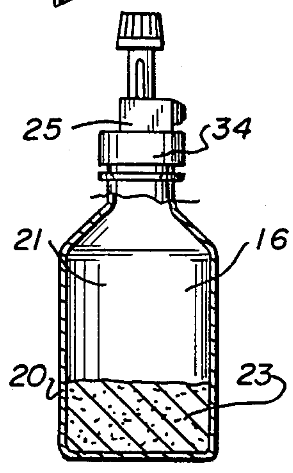
FIG. 3 is side view of a drug storage receptacle shown in FIG. 1 as one of the packaged components.
Figure 2:
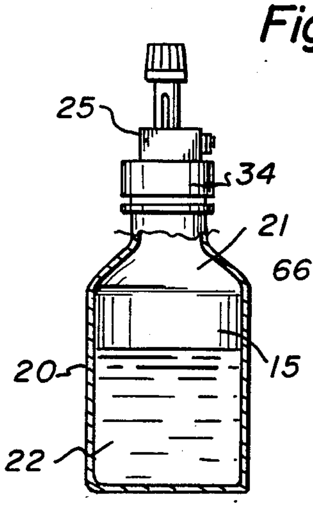
FIG. 2 is a side view of a diluent storage receptacle shown in FIG. 1 as one of the packaged components.

First substance storage receptacle 15 is shown in greater detail in FIG. 2, while second substance storage receptacle 16 is shown in greater detail in FIG. 3. As can be appreciated, these receptacles can be identical and may be, for example, vials of any suitable material, such as, again by way of examples, glass, polypropylene, polyethylene, or laminates. Each vial 15 and 16 has a body portion 20 defining a storage chamber, or reservoir, 21, which retains the desired substance, such as a diluent 22 (as indicated in FIG. 2) or a drug 23 (as indicated in FIG. 3) where a drug is to be mixed with diluent to reconstitute the drug.

Figure 4:
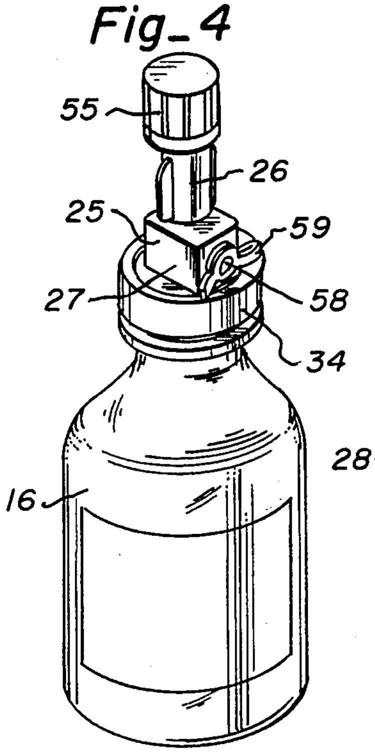
FIG. 4 is a perspective view of the storage receptacle having a transfer unit mounted thereon.
Figure 5:
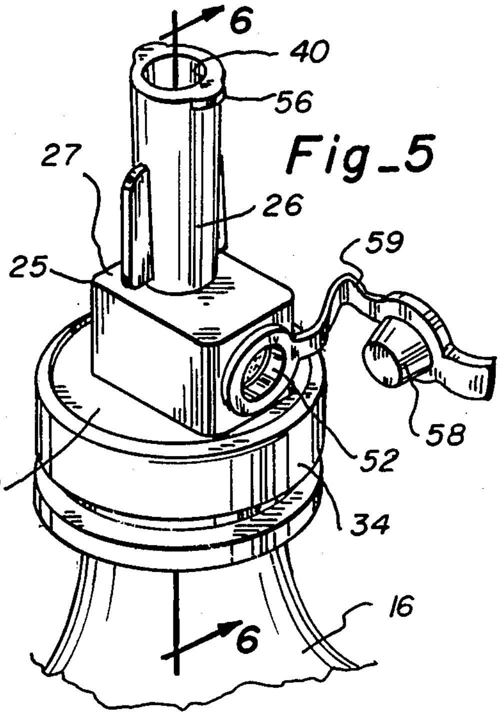
FIG. 5 is an enlarged perspective view illustrating primarily the transfer unit shown in FIG. 4.
Figure 6:
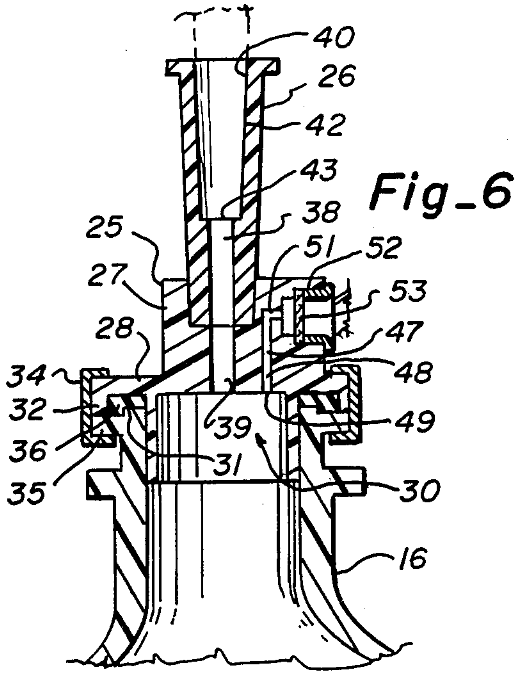
FIG. 6 is a sectional view taken through lines 6—6 of FIG. 5 and illustrating the transfer unit in greater detail.

Each vial 15 and 16 has a transfer unit 25 connected therewith, and the transfer units may be identical, with transfer unit 25 being shown in greatest detail in FIGS. 4 through 6.

As best shown in FIGS. 4 through 6, transfer unit 25 includes upper and lower body portions 26 and 27. Lower body portion 27 has disk 28 mounted thereon, which disk is of a size to span and cover aperture 30 defined by upper annular lip 31, which lip forms the mouth of the vial (i.e., vial 15 or 16 with vial 16 being illustrated in FIGS. 4 through 6).

Disk 28 preferably has a depending shoulder 32 which snugly fits over the outer wall of lip 31. If desired (and as shown), a clamp ring 34 may be provided around the edge of disk 28 and outwardly directed shoulder 35 of the vial to hold the transfer unit against and over the mouth of the vial (alternately, welding could be utilized if the vial is formed of plastic material), and a gasket ring 36 may be positioned between lip 31 of the vial and the inner surface of disk 28 to assure establishment of a seal therebetween.

Transfer unit 25 may be formed of any suitable material, such as plastic, for example, and has a central bore 38 therethrough. Bore 38 has an inner port 39, which inner port opens through disk 28 into the reservoir formed within the storage receptacle, and an outer port 40, at upper body portion 26, with outer port 40 being preferably adapted to receive a portion 42 of delivery receptacle 14 having an opening 43 therein in order to establish communication, through bore 38, between the storage receptacle reservoir and the compartment, or reservoir, 44 in delivery receptacle 14.

As specifically shown in FIGS. 1 and 7 through 9, delivery receptacle 14 is embodied as a syringe with compartment 44 being formed by syringe body 45. End, or nozzle, portion 42 of syringe 14 is preferably tapered, and is snugly received in port 40 of transfer unit 25 so that the long and preferably elastomeric insert of end portion 42 forms a seal with the inner walls of port 40 (as indicated in FIG. 6).

Lower, or main, body portion 27 of transfer unit 25 has a vent passage, or bore, 47 therein, which vent passage has an inner conduit 48 with port 49 at the inner end thereof, which port opens through disk 28 into the reservoir of the storage receptacle. As shown in FIG. 6, conduit 48 of vent passage 47 is parallel to, but radially offset from, central bore 38 so that ports 39 and 49 are adjacent to, but spaced from, one another. The openings into the reservoir are preferably flash-free.

The outer conduit 51 of vent passage 47 extends outwardly, at substantially a right angle, from the end of conduit 48 so that conduit 51 opens to the side of main body portion 27 of the transfer unit. As best shown in FIG. 6, the outer portion 52 of conduit 51 has an enlarged diameter relative to the remainder of the conduit, and is of a sufficient size to snugly receive filter 53 therein.

Filter 53 is a two-way filter that is air permeable (but is impermeable to liquid and solid materials), with the filter being a hydrophobic (rather than hydrophilic), sterile bacterial filter having, for example, a 0.22 micron pore size.

Cap 55 (as best shown in FIG. 4) is provided at the end of port 40 at the outer end of central bore 38, and lugs 56 (as best shown in FIG. 5) are provided to releasably lock the cap in position to seal the central bore. In addition, plug 58 is provided for insertion into the vent outer port formed at the end of enlarged bore conduit 52 outwardly of filter 53. When in position in the end of the vent passage (as indicated in FIG. 4), a seal is provided thereat. As indicated, plug 58 may also have a retainer strap 59 thereon for retaining the plug adjacent to the transfer unit when the plug is withdrawn from the position sealing the end of the vent passage (as indicated in FIG. 5).

Delivery receptacle 14 has an actuator 61 therein for causing positive movement of the stored substance to achieve mixing, and then later, delivery of the mixture. As specifically shown in FIGS. 7 through 9, actuator 61 can be a piston within syringe body portion 45, and piston 61 is actuated by rod 62, the outer end portion 63 of which rod extends from the rear end of the syringe (i.e., opposite to that of front, tapered end 42).

In preparing a package, storage receptacles 15 and 16 (if utilized) are pre-filled (with diluent and a drug, for example) and a transfer unit 25 is connected with each of the receptacles to seal the same material needed. A syringe, with a cap 65 on the tapered end portion 42, is also provided, and the components are positioned in the package, and the package then sealed, as indicated in FIG. 1. The package is then retained in sealed condition, preferably until needed for use. The components used in the package may be varied, as brought out above, and, alternately, for example, the syringe may be filled with one of the substances (such as diluent) which would then allow one of the storage receptacles to be deleted from the package.

Figure 7:
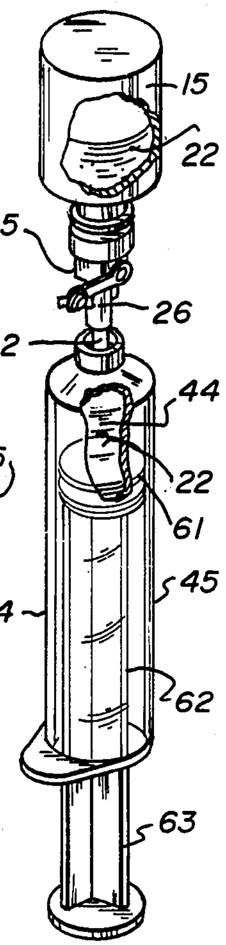
FIG. 7 is a perspective view of a syringe and diluent storage receptacle illustrating insertion of diluent into the delivery receptacle.

To use the package, the user opens the package and, using sterile procedures, attaches the delivery component (a syringe as specifically described herein) to the diluent vial 15, after removing the connector cap 55 of the vial. Vent plug 58 is also removed, and after inverting the syringe and vial, as indicated in FIG. 7, the diluent is drawn from the vial into the syringe by moving piston 61 rearwardly within syringe body 45. Vent 47 allows air to enter vial 15 through filter 53, thus preventing a vacuum from forming and hindering diluent removal.

Figure 8:
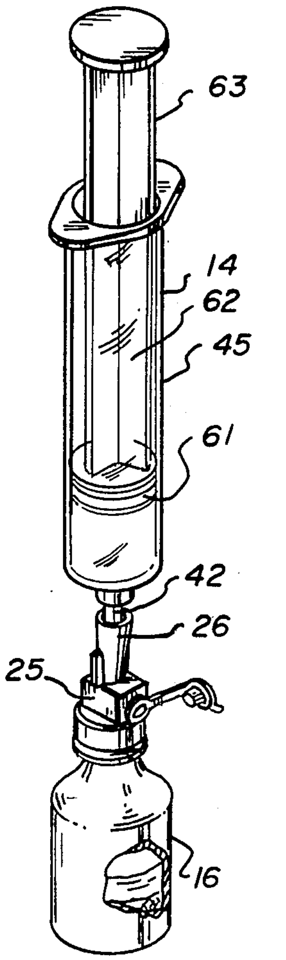
FIG. 8 is a perspective view of a syringe and drug storage receptacle illustrating insertion of diluent from the delivery system into the drug storage receptacle for mixing thereat.

When syringe 14 is filled with diluent (or alternately when using a syringe having diluent already stored in the syringe), the user removes cap 55 and vent plug 58 from drug vial 16, and attaches the filled syringe to transfer unit 25 on drug vial 16. The user then injects the diluent from syringe 14 into vial 16, as indicated in FIG. 8, by moving the piston within the syringe body forwardly (toward the nozzle of the syringe), to mix the contents to dissolve the drug (which drug is preferably in solid form but could be in liquid form) in the liquid diluent. Filter 53 in vent 47 allows air in the vial to escape, and thus prevents pressure entrapment. Vent 47 also allows gaseous by-products of the salvating reaction (if any) to escape without contaminating the user with aerosol of drug, which might be hazardous to the user.

Figure 9:
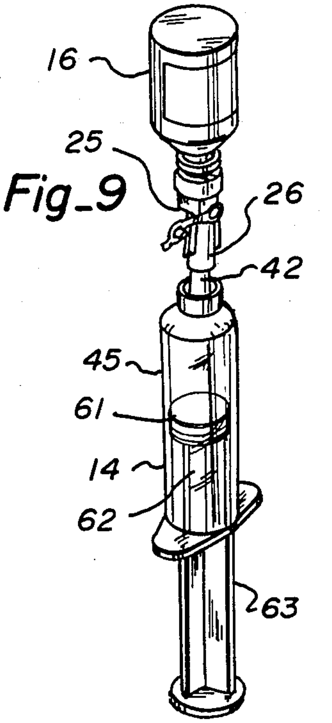
FIG. 9 is a perspective view of a syringe and drug storage receptable illustrating withdrawal of the mixture from the storage receptacle into the delivery receptacle.

After shaking vial 16, if necessary, to completely dissolve the drug (if in solid form), and after inverting the syringe and vial, as indicated in FIG. 9, the user then draws the contents of vial 16 into syringe 14 by actuation of syringe piston 61 rearwardly within syringe body 45 (i.e., piston 61 is moved in the axial direction opposite to that of the initial movement). The vent on the drug vial now allows sterile air to enter the vial and the liquid in the vial to be drawn into this syringe.

The syringe is now filled with reconstituted drug solution, and the user removes syringe 14 from transfer unit 25 (and hence also from drug vial 16) and may, at this time, dispose of the emptied vials and transfer units.

Figure 10:
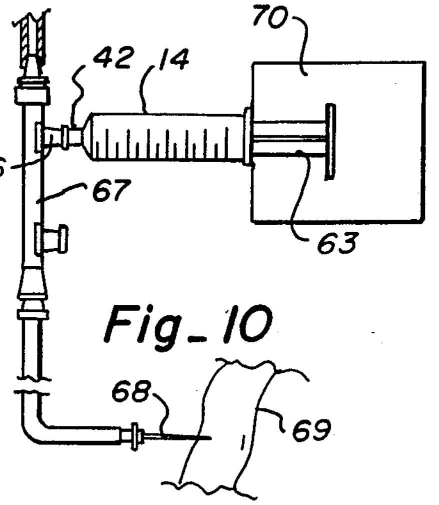
FIG. 10 is a perspective view illustrating typical use of the delivery receptacle in delivering a reconstituted drug to a patient.

The syringe with the reconstituted drug therein may then be utilized as, for example, by connecting the syringe through a secondary fluid access port 66 (unused secondary fluid access ports are maintained closed), to primary fluid conduit 67, which primary conduit can be connected to deliver a primary fluid therethrough (as is conventional), as indicated in FIG. 10. As shown, tube 67 extends to needle 68 insertable into a member (such as arm 69) of a patient. Syringe 14 may be manually operated, or, preferably, may be inserted into a delivery control device 70, which device is connected with outer portion 63 of rod 62 to control actuation of pistion 61 to thereby achieve individualized dose administration to a patient. Such a delivery control device is shown in U.S. patent application Ser. No. 734,028 entitled "Syringe Drive Apparatus and Method", filed May 5, 1985, by David C. Howson et al, and assigned to the assignee of this invention.

As can be appreciated from the foregoing, this invention provides an improved apparatus and method for handling substances, and particularly drugs.

What is claimed is:

1. A substance handling apparatus, comprising:

receptacle means having a storage chamber for receiving a first substance, said receptacle means having a first chamber opening at one portion thereof;

delivery means having a delivery chamber for receiving a second substance, said delivery means having a second chamber opening at one portion thereof;

transfer means sealingly engagable with said first chamber opening of said receptacle means and having a first conduit therein opening to first and second spaced ports, said transfer means permitting substance flow between said storage chamber and said delivery chamber through said first conduit when said transfer means is positioned with said first and second chamber openings in communication with said first and second ports, said transfer means also having a second conduit therein opening to third and fourth spaced ports with said third port being in communication with said storage chamber when said first spaced port is in communication with said storage chamber, with said fourth port opening externally of said storage chamber, and with said second conduit having filter means therein for permitting passage of air in either direction through said second conduit but substantially blocking passage of liquid and solid materials in either direction through said second conduit; and actuating means at least partially within said delivery chamber to cause, when said first and second chamber openings are in communication with said first and second ports, positive movement of said second substance from said delivery chamber to said storage chamber through said conduit upon actuation of said actuating means in one predetermined direction so that said first and second substances can be mixed within said storage chamber, and to cause positive movement of said mixture of said first and second substances from said storage chamber to said delivery chamber through said conduit upon actuation of said actuating means in a second predetermined direction, said actuating means also causing positive delivery of said mixture of said first and second substances from said delivery means upon actuation of said actuating means when said mixture is within said delivery chamber.

2. The apparatus of claim 1 wherein said delivery means includes a syringe body, and wherein said actuating means includes a piston within said syringe body.

3. The apparatus of claim 1 wherein said actuating means includes means for actuating said piston in said one predetermined direction within said syringe body to cause flow of said second substance from said delivery chamber to said storage chamber, for actuating said piston in said second predetermined direction opposite to said one direction within said syringe body to cause flow of said mixture of said first and second substances from said storage chamber to said delivery chamber, and for actuating said piston within said syringe body in said one direction to cause flow of said mixture of said first and second substances from said delivery means.

4. The apparatus of claim 1 wherein said substance handling apparatus is for mixing substances at least one of which includes a drug, and wherein said apparatus includes means for maintaining sterile conditions during transfer and mixing of said substances.

5. The apparatus of claim 4 wherein at least one of said receptacle means and said delivery means has sufficient size to enable said apparatus to be utilized for multi-dose application.

6. The device of claim 1 wherein said apparatus includes second receptacle means for storing said second substance, and wherein said apparatus includes second transfer means connectable between said second receptacle means and said delivery means for allowing transfer of said second substance to said delivery means through said second transfer means.

7. The substance handling apparatus of claim 1 wherein said filter means is a one-piece micropore, hydrophobic filter.

8. The substance handling apparatus of claim 7 wherein said filter means has a pore size of about 0.22 microns.

9. A drug handling apparatus, comprising:

a receptacle forming a reservoir for receiving one of a drug and a diluent therein, said receptacle having a reservoir access opening at one portion thereof;

a syringe having a body portion forming a compartment for receiving the other of said drug and diluent, a piston within said body portion, and a compartment access opening at one end; and a transfer element having a body portion with a first conduit therein opening to first and second spaced ports, said body portion being sealingly engageable with said reservoir access opening to enable communication of said first port with said receptacle reservoir when so positioned, said body portion also being adapted for sealing engagement with said syringe body to establish communication of said second port with said syringe compartment access opening so that, when so positioned, said one of said drug and diluent in said syringe compartment is caused to be moved from said compartment to said storage reservoir by actuation of said syringe piston in one direction so that said drug and diluent are mixed in said storage receptacle, and so that said mixture of said drug and diluent is caused to be moved from said receptacle reservoir to said delivery compartment by actuation of said syringe piston in the direction opposite to that of said one direction, and so that, after removal of said transfer means and receptacle from said syringe, said mixture is discharged from said syringe through said compartment access opening upon actuation of said syringe piston in said one direction, and said transfer element also including a second conduit having third and fourth spaced ports and a filter, said third port being in communication with said receptacle reservoir when said transfer element is in said sealing engagement with said receptacle, with said fourth port opening externally of said transfer element, and with said filter being within said second conduit for permitting passage of air in either direction through said second conduit but substantially blocking passage of liquid and solid material in either direction through said second conduit.

10. The apparatus of claim 9 wherein said apparatus includes a second receptacle like that of said first receptacle for receiving a diluent, and wherein said apparatus also includes a second transfer element like that of said first transfer element whereby said diluent may be transferred to said syringe by positioning the outer port of said second transfer element in sealing engagement with said second receptacle and said syringe to establish communication of said second receptacle reservoir with said syringe compartment through the conduit in said second transfer element.

11. A method for handling of substances, said method comprising:

providing a delivery chamber having an access opening and an actuator at least partially within the delivery chamber;

introducing a first substance into said delivery chamber;

providing a storage reservoir having an access opening and a second substance within the storage reservoir;

providing a transfer element sealingly engagable with said access opening of said storage reservoir;

providing an air passage through said transfer element permitting air flow to and from said storage receptacle but substantially blocking passage of liquid and solid material to end from said storage receptacle;

establishing a flow path through said transfer element extending between the access openings of said storage reservoir and said delivery chamber;

moving said actuator to thereby cause positive flow of said first substance from said delivery chamber to said storage reservoir through said established flow path;

mixing said first and second substances at said storage reservoir;

moving said actuator to thereby cause positive flow of the mixture of said first and second substances from said storage reservoir to said delivery chamber through said established flow path;

terminating said established flow path between the access openings of said storage reservoir and said delivery chamber; and moving said actuator to thereby cause positive flow of the mixture of said first and second substances through said access opening of said delivery chamber to a patient when connected with said delivery chamber.

12. The method of claim 11 wherein providing the delivery chamber and actuator includes providing a syringe having a piston therein.

13. The method of claim 11 wherein at least one of said substances to be mixed is a drug, and wherein said flow path is established in a closed pathway to maintain sterile conditions.

14. The method of claim 11 wherein said method includes repeatedly establishing said flow path between said storage reservoir and said delivery chamber whereby said mixture of said substance can be repeatedly withdrawn from said storage reservoir to said delivery chamber to a patient connected therewith.

15. The method of claim 10 wherein said method includes providing a second reservoir having said first substance therein, and introducing said first substance into said delivery chamber by establishing a flow path therebetween prior to establishing said flow path for said first substance from said delivery chamber to said first reservoir.

16. A method for handling drugs requiring mixing prior to delivery of the resulting mixture from a syringe to a patient, said method comprising:

providing a liquid diluent storage receptacle;

transferring liquid diluent in said storage receptacle into the reservoir of a syringe having a syringe piston therein, which reservoir opens from the syringe through a tapered opening at one end thereof;

providing a storage chamber having a drug stored therein and an outlet opening;

establishing a flow path from said outlet opening of said storage chamber to said tapered opening of said syringe;

actuating said syringe piston in one direction to cause diluent to flow from said syringe reservoir to said storage reservoir with said discharged diluent flowing through said syringe opening, established flow path, and chamber outlet opening to the storage chamber;

mixing said drug with said diluent at said storage chamber;

actuating the syringe piston in a direction opposite to said one direction to cause withdrawal of the mixture of said drug and diluent from said storage chamber with said withdrawn mixture flowing through said chamber output opening, established flow path, and syringe opening to said syringe reservoir;

terminating said flow path between said storage chamber and said syringe reservoir; and actuating said syringe piston in said one direction to cause delivery of said mixture from said syringe reservoir to a patient when connected therewith.

* * * * *

UNITED STATES PATENT AND TRADEMARK OFFICE
CERTIFICATE OF CORRECTION

PATENT NO. : 4,722,733

DATED : February 2, 1988

INVENTOR(S) : Howson

It is certified that error appears in the above-identified patent and that said Letters Patent is hereby corrected as shown below:

Column 9, line 57, "end" should be --and--.

Signed and Sealed this

Sixth Day of September, 1988

*Attest:*

DONALD J. QUIGG

*Attesting Officer*

*Commissioner of Patents and Trademarks*